(12) United States Patent
Oben

(10) Patent No.: US 8,361,523 B2
(45) Date of Patent: Jan. 29, 2013

(54) **EFFECTS OF *HYPODAPHNIS ZENKERI* ON VARIOUS CARDIOVASCULAR RISK FACTORS AND METABOLIC SYNDROME**

(75) Inventor: Julius Enyoug Oben, Cameroon (CM)

(73) Assignee: Gateway Health Alliances, Inc., Fairfield, CA (US)

( * ) Notice: Subject to any disclaimer, the term of this patent is extended or adjusted under 35 U.S.C. 154(b) by 0 days.

(21) Appl. No.: 13/557,000

(22) Filed: Jul. 24, 2012

(65) Prior Publication Data

US 2012/0288576 A1 Nov. 15, 2012

Related U.S. Application Data

(63) Continuation of application No. 12/901,480, filed on Oct. 8, 2010, now Pat. No. 8,241,682.

(60) Provisional application No. 61/249,904, filed on Oct. 8, 2009.

(51) Int. Cl.
*A01N 65/00* (2009.01)
*A61K 36/48* (2006.01)
*A61K 36/00* (2006.01)

(52) U.S. Cl. ......... 424/757; 424/776; 424/725; 514/909

(58) Field of Classification Search .................. None
See application file for complete search history.

(56) References Cited

PUBLICATIONS

Tan et al. (2006) Pharmacologyonline 3: 877-891.*
Kuate et al. (2010) Effects of Dichrostachys glomerata spice on cardiovascular diseases risk factors in normoglycemic and type 2 diabetic obese volunteers, Food Research International, doi: 10.1016/j.foodres.2010.09.037.*

* cited by examiner

*Primary Examiner* — Chris R Tate
*Assistant Examiner* — Russell Fiebig
(74) *Attorney, Agent, or Firm* — Steve P. Hassid; Silicon Edge Law Group, LLP

(57) ABSTRACT

Methods of improving a variety of health related factors including, but not limited to weight, cholesterol levels, triglyceride levels and HDL levels, is provided. In one embodiment, a method of reducing body weight in an overweight subject is provided; the method comprises administering a composition containing an effective amount of *Hypodaphnis zenkeri*, to an overweight subject, whereby the administering of the composition to the overweight subject is effective in reducing bodyweight in the overweight subject.

7 Claims, 19 Drawing Sheets

EFFECTS OF *HYPODAPHNIS ZENKERI* ON VARIOUS CARDIOVASCULAR RISK FACTORS AND METABOLIC SYNDROME

CROSS REFERENCE TO RELATED APPLICATIONS

The present application is a continuation of U.S. Non-Provisional patent application Ser. No. 12/901,480 filed on Oct. 8, 2010, which claims benefit to the U.S. Provisional Patent Application No. 61/249,904, filed on Oct. 8, 2009, both of which are hereby incorporated by reference in their entirety.

FIELD OF THE DISCLOSURE

The present disclosure relates generally to the effects and benefits of *Dichrostachys glomerata* (DG), *Hypodaphnis zenkeri* (HZ), and *Xylopia aethiopica* (XA) a variety of health related factors in a mammal. More specifically, the present disclosure relates to methods and compositions for using *Dichrostachys glomerata* (DG), *Hypodaphnis zenkeri* (HZ), and *Xylopia aethiopica* (XA) to improve a various cardiovascular risk factors and metabolic syndrome of a mammal.

BACKGROUND

*Dichrostachys glomerata* (DG) is a semi-deciduous to deciduous tree up to 7 meters tall with an open crown. Bark on young branches appear green and hairy but dark grey-brown and longitudinally fissured on older branches and stems; smooth on spines formed from modified side shoots. *Hypodaphnis zenkeri* (HZ), is a lower storey tree of the lowland rain-forest to 17 m high by 1.60 m in girth, occurring in S. Nigeria and W. Cameroon, and in E. Cameroun and Gabon. The heart-wood is a good timber, grey to dark chestnut color and easy to work. *Xylopia aethiopica* (XA) is is an evergreen, aromatic tree, growing up to 20 m high. It is a native to the lowland rainforest and moist fringe forests in the savanna zones of Africa.

Obesity and its related complications (cardiovascular disease, type 2 diabetes, hypertension etc) are on the increase worldwide. The purpose of this study was to assess the effects of nutritional supplementation with three spices *Dichrostachys glomerata* (DG), *Hypodaphnis zenkeri* (HZ), and *Xylopia aethiopica* (XA) on cardiovascular risk factors in obese subjects.

Obesity can be attributed to complex physiological, genetic, cultural and psychological factors. Despite a growing awareness of the detrimental effects of excessive body fat on health, obesity remains a major public health problem in the world.

Numerous epidemiologic studies have demonstrated that, obesity itself is an independent risk factor for type 2 diabetes and coronary heart disease (Colditz, et al., 1995; Chan et al., 1994), and is associated with increased morbidity and mortality risk (Adams et al., 2006). Cardio-metabolic risk as defined by metabolic syndrome is characterized by the presence of abdominal obesity, atherogenic dyslipidemia, hypertension, insulin resistance or glucose intolerance, pro-thrombotic states, and pro-inflammatory states (Aronne, 2006). These concomitant abnormalities which often occur in obesity magnify the risk of cardiovascular disease and require aggressive management of all cardiovascular risk factors. This includes the lifestyle modification treatment plans and pharmacological therapies (Aronne, 2006). A widely held view, which has not been subjected to rigorous critical evaluation in large-scale prospective studies, is that modest (approximately 5%-10%) intentional weight loss is associated with significant improvements in obesity-related cardiovascular and metabolic abnormalities (Golstein, 1992; Williamson, 1997). The current pharmacotherapy that target cardiovascular and metabolic risk include drugs which promotes weight loss and improves metabolic risk factors and others drugs, which reduce metabolic risk factors without treating obesity. Such drugs are expensive, have a variety of negative side effects, often are less effective over time and provide different results for different people, thus encouraging investigation of new dietary supplements as therapy.

Spices are amongst the thousands of food flavoring substances used worldwide (Cadby, 2004). They have also been used for generations, as components of traditional medicines (lai and Roy, 2004). There is scientific evidence to support the fact that, several spices possess beneficial physiological effects which can have potential therapeutic applications in a variety of disease conditions (Peter, 2006). The components of spices responsible for the quality attributes have been designated as "active principles," and in many instances, they are responsible for the observed beneficial physiological effects. Spices are generally rich in protein, with the ash content varying from 2.3% in marjoram to 16.7% in basil leaves. Some spices contain significant levels of vitamins and minerals, which cannot be ignored. A few spices are also rich sources of dietary fibres (Srinivasan, 2005). Both animal and human studies have unequivocally demonstrated the hypocholesterolemic effects of spices (Srimal, 1997).

In a recent study, dietary supplementation with aged garlic extract showed better beneficial effects, relative to fresh garlic, on the lipid profile and blood pressure of moderately hypercholesterolemic subjects (Steiner et al., 1996). The antioxidant properties of several spice principles were investigated in rats by measuring the lipid peroxidation induced both in vivo and in vitro (Joe & Lokesh, 1994; Reddy & Lokesh, 1994).

SUMMARY OF THE INVENTION

In one embodiment of the present disclosure, a method of reducing bodyweight in an otherwise healthy overweight subject, the method comprising: administering a composition containing an effective amount of *Hypodaphnis zenkeri* to the overweight subject.

In another embodiment of the present disclosure, a method of reducing bodyweight in an otherwise healthy overweight subject, wherein the effective amount is 200 mg to 6000 mg to the overweight subject per day.

In yet another aspect of at least one embodiment of the present disclosure, a method of reducing bodyweight in an otherwise healthy overweight subject, wherein the composition comprises the seed of the *Hypodaphnis zenkeri*.

In yet another aspect of at least one embodiment of the present disclosure, a method of reducing bodyweight in an otherwise healthy overweight subject, wherein the composition comprises the bark of *Hypodaphnis zenkeri*.

In yet another aspect of at least one embodiment of the present disclosure, a method of reducing bodyweight in an otherwise healthy overweight subject, wherein the composition comprises ground-up *Hypodaphnis zenkeri* plant.

In yet another aspect of at least one embodiment of the present disclosure, a method of reducing bodyweight in an otherwise healthy overweight subject, wherein the composition comprises the pods of *Hypodaphnis zenkeri*.

In yet another aspect of at least one embodiment of the present disclosure, a method of reducing bodyweight in an otherwise healthy overweight subject, wherein the pods are dried ground pods.

BRIEF DESCRIPTION OF DRAWINGS

The drawings disclose illustrative embodiments and represent graphical summaries of the data explained and described herein. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

The above-mentioned features and objects of the present disclosure will become more apparent with reference to the following description taken in conjunction with the accompanying drawings and in which.

Figure 1A:
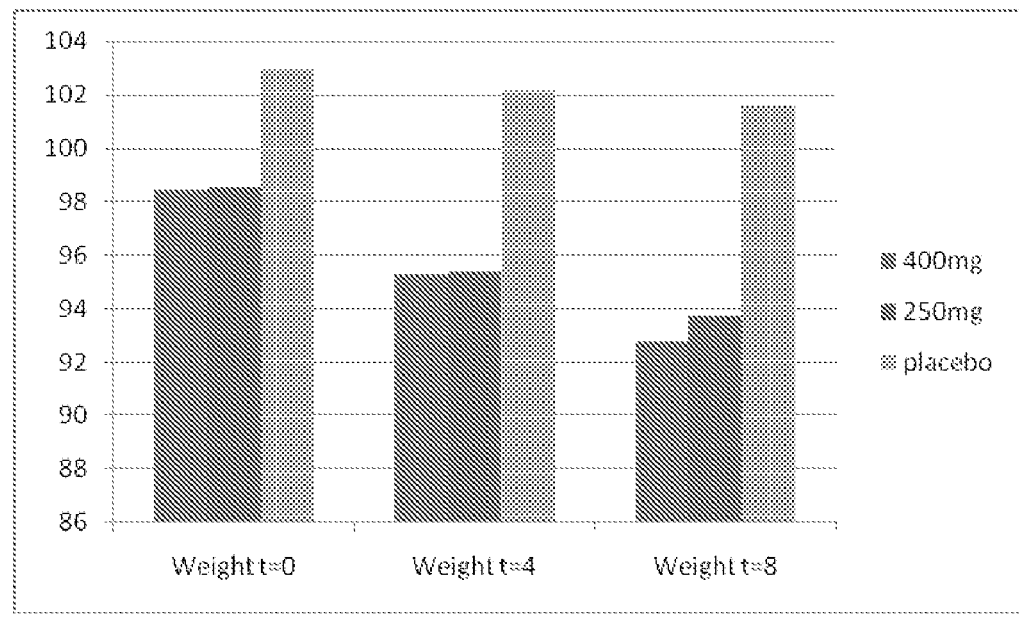
FIGS. 1A and 1B are bar graph charts which graphically demonstrate the results of weight change after administering DG as part of the experiments described herein.

It should be appreciated that, where T0, T4 and T8 values are represented in the Figures, positive values means the parameter is decreasing from T0 to T4 or from T0 to T8 and negative values means the parameter is increasing from T0 to T4 or from T0 to T8.

DETAILED DESCRIPTION OF ILLUSTRATIVE EMBODIMENTS

*Dichrostachys glomerata*, *Hypodaphnis zenkeri*, and *Xylopia aethiopica* are three spices commonly used in the Cameroonian cuisine and are also used in traditional Cameroonian medicine as natural remedy for many illness. One aim of the study disclosed herein was to investigate the effects of these spices on weight loss and various cardiovascular risk factors and metabolic syndrome in obese individuals.

To determine the efficacy and effectiveness of each of *Dichrostachys glomerata* (DG), *Hypodaphnis zenkeri* (HZ), and *Xylopia aethiopica* (XA) on a mammal, sixty three adult obese subjects (25-60 years; BMI 27-40) were given a daily dose of either 250 mg or 400 mg capsules of one of the three powdered *Dichrostachys glomerata* (DG), *Hypodaphnis zenkeri* (HZ) or *Xylopia aethiopica* (XA) spice compositions for 8 weeks. Anthropometric measurements and fasting blood samples were taken at baseline and again after 4 and 8 weeks of supplementation to determine the effectiveness of each composition on the mammal.

After 8 weeks of treatment, all the treated groups lost weight, but the changes were not significant in the XA group when compared to the placebo group. Triglyceride levels were reduced ($P<0.05$) by the two doses of DG after 4 weeks but only by the lower dose (250 mg) of HZ after 8 weeks of treatment. The three spices brought about significant reductions in total cholesterol which was accompanied by a significant increase in HDL-cholesterol, while the fasting blood glucose was reduced by XA and DG, with the lower dose being more effective.

The results of the study demonstrated that *Dichrostachys glomerata*, *Hypodaphnis zenkeri*, and *Xylopia aethiopica* supplementation decreased plasma lipids, body weight and fasting blood glucose concentrations in obese human subjects. These three spice compositions, which are commonly used in Cameroonian cuisine, appear to be beneficial in reducing weight as well as lipid parameters linked to cardiovascular diseases.

Participants for the study were recruited from the city of Yaounde, Cameroon and surrounding metro region through radio and print media advertisement. Participants were male or female, ages 25-60. In addition, participants met at least three of the following criteria: The BMI of participants ranged from 27 to 40, and their weights ranged from 70 to 120 kg. After physical examination, participants suffering from diabetes mellitus requiring daily insulin management, pregnant or lactating, as well as those on any form of weight, cholesterol, or inflammation-reducing medication were excluded from the study. Also excluded were participants involved in intense exercise programs, those who had medical conditions known to affect serum lipids or those who had a history of drug or alcohol abuse. In general, participants included in the study had (1) good health free from significant medical illness that, in the opinion of the investigator, could adversely compromise study participation for any reason; (2) stable body weight (+/−2 kg) for at least three months prior to the study randomization without use of medication known or suspected to affect body weight or appetite; (3) no concomitant or recent (within the past three months) bacterial or seasonal viral infection (e.g. influenza); (4) no attempts at weight loss through dietary intervention over the three months prior to trial randomization; (5) no participation in a structured weight control program for at least three months prior to study randomization; (6) non-smoker; (7) capability and willingness for multiple blood sampling procedures; and (8) ability to competently understand and sign the consent form.

No major dietary intervention or formal physical activity program was instituted during the course of the study; participants were instructed to maintain the current level of physical activity prior to study randomization during the course of the study.

The study was approved by the University of Yaounde Internal Review Board. The purpose, nature and potential risks of the study were explained to all participants, who gave their written informed consent before participation. The study was conducted in accordance with the Helsinki Declaration (1983).

All test materials were bought from the local market in Yaounde. Dried pods (DG), bark (HP) and fruits (XA) were ground and encapsulated in individual packets of capsules for each of the three spices. The identical-looking placebo and active formulation capsules contained, respectively, maize-based powder consisting of 250 or 400 mg maltodextrin.

The study was a randomized, double-blind, placebo-controlled design for 8 weeks. A total of 63 overweight or obese participants completed the study (70%). The volunteers were randomly divided into seven groups—placebo, 250 mg *Dichrostachys glomerata* (DG 1), 400 mg *Dichrostachys glomerata* (DG2), 250 mg *Hypodaphnis zenkeri* (HP1), 400 mg *Hypodaphnis zenkeri* (HP2), 250 mg *Xylopia aethiopica* (XA1) and 400 mg *Xylopia aethiopica* (XA2). The participants consumed a capsule of either placebo or spice 30-60 minutes before lunch and dinner throughout the study period.

Anthropometric measurements were takes as follows. Height was measured with a wall-mounted stadiometer (Seca Model 240 Stadiometer). Body weight and percentage body fat, were assessed using a Tanita™ BC-418 Segmental Body Composition Analyzer/Scale that uses bio-electrical impedance analysis for body composition analysis. BMI was calculated as the ratio of weight in kilograms to the height in meters square. Waist circumference measurements to the nearest 0.1 cm were taken at the mid-point between the bottom rib and the hipbone, without restrictive garments using a flexible non-expandable tape measure.

Sample collection: Fasting blood samples (5 ml of blood) were collected at baseline, and at 4, and 8 weeks. Serum obtained from each blood sample was split into multiple 500 µl aliquots and stored at −20° C. until needed for the measurement of total cholesterol, LDL cholesterol, fasting blood glucose levels.

Determination of glucose in blood using glucose oxidase with an alternative oxygen receptor was adopted for this study (Trinder P, 1969). Serum total cholesterol was assayed by the cholesterol oxidase method (Richmond W, 1973), while triglycerides as well as serum glucose levels were assayed following the method described by Buccolo G., David H, (1973). HDL cholesterol was determined using a heparin manganese precipitation of Apo B-containing lipoproteins (Bachorik et al., 1976). LDL cholesterol was calculated using the Friedewald formula (Friedewald et al., 1972).

The data were recorded as mean±standard deviation, and analyzed by a commercial software package (SPSS version 10.5 for Windows, SPSS Inc.). One-way analysis of variance was performed by ANOV A procedures. Significant differences between means of percentages of change were determined by Student's t-test for normal distribution or the Mann-Whitney test for non-normal distribution. P-Values $<0.05$ were regarded as significant and p-values $<0.01$ were very significant.

In a second related study, the effect of DG on various cardiovascular and health related parameters was also determined. DG or *D. glomerata* penetrates clear-cut areas far into the rainforest zone. In Malaysia, it occurs in areas with strong seasonal climate, usually on poor, occasionally clayey soils, in brushwood, thickets, hedges, teak forest and grassland. Forms dense hammocks on lateritic soils in Senegal and Sudan, while in India it occurs in dry deciduous forest.

Fruit and seeds from *D. glomerata* are edible. Fodder: Cattle, camels and game (giraffe, buffalo, kudu, Lichtenstein's hartebeest, nyala, impala, klipspringer, red duiker and Damara dik-dik) relish the juicy pods that drop to the ground and even eat the young twigs and leaves. Leaves are highly palatable, rich in protein (11-15% crude protein) and mineral content. Young shoots and pods are also browsed by smaller domestic animals. Pods and seeds do not contain hydrocyanic acid, minimizing the chance of poisoning animals.

The bark of DG is used to treat dysentery, headaches, toothaches, elephantiasis and acts as a vermifuge. Root infusions are taken for leprosy, syphilis coughs, as an anthelmintic, purgative and strong diuretic. Pounded roots and leaves are used to treat epilepsy. The roots are chewed and placed on the sites of snakebites and scorpion stings, and the leaves, which are believed to produce a local anesthesia, are used for the same purpose and also as a remedy for sore eyes and toothache. Leaves are taken as a diuretic and laxative, and used for gonorrhea and boils; powder from leaves is used in the massage of fractures. The plant is used as a veterinary medicine in India.

Initial work on the DG seed, which is a commonly used spice has been carried out in the lab of Dr. Oben's lab as part of a Ph.D. thesis. Extensive in vitro and in vivo (mainly animal) work has been done with this spice.

Figure 1B:
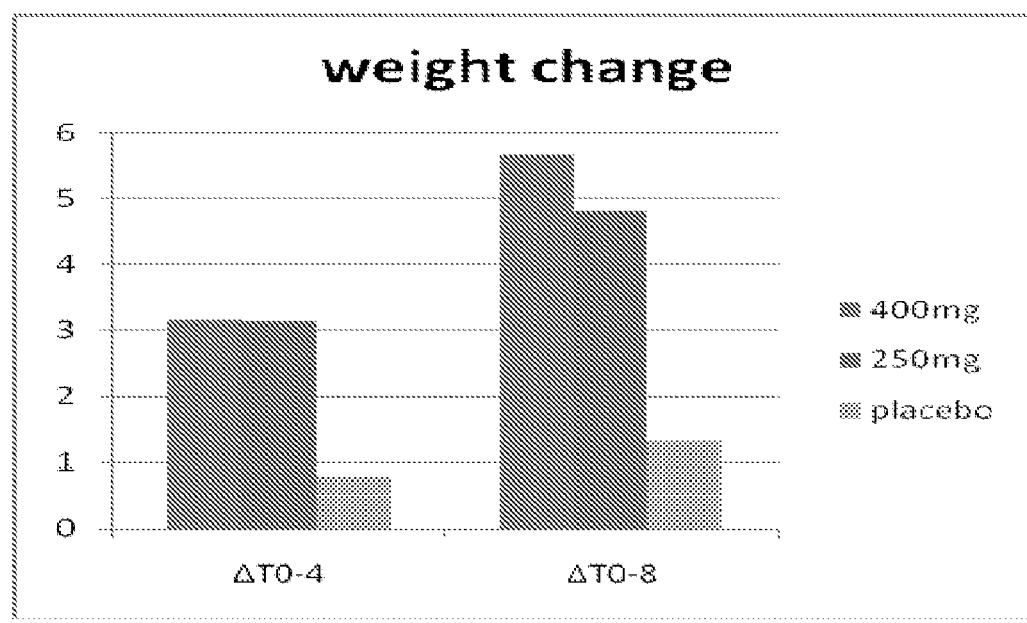
Figure 2A:
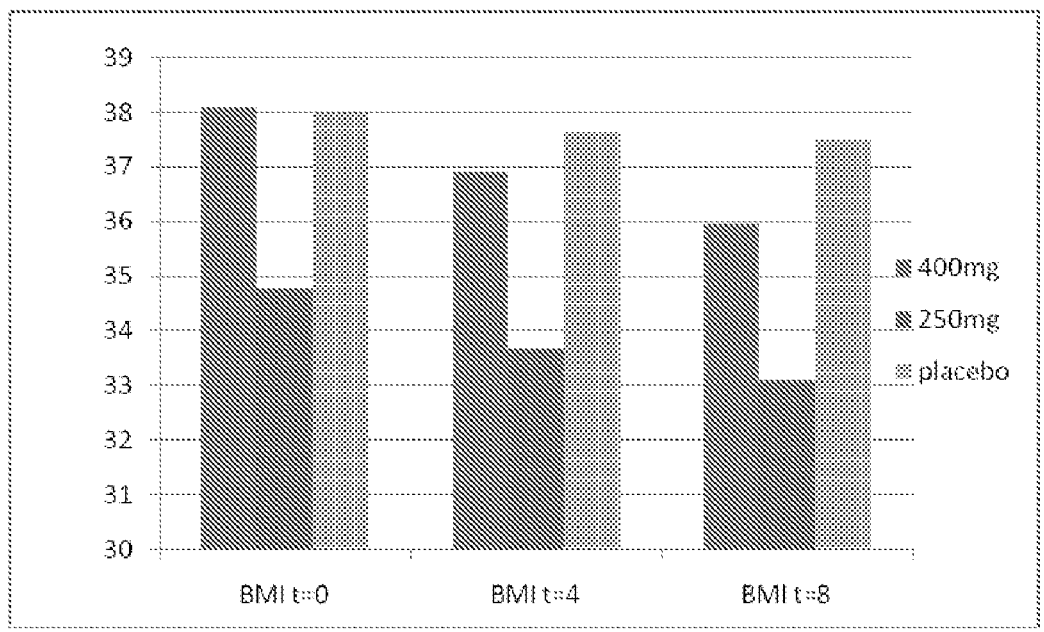
FIGS. 2A and 2B are bar graph charts which graphically demonstrate the results of BMI change after administering DG as part of the experiments described herein.
Figure 2B:
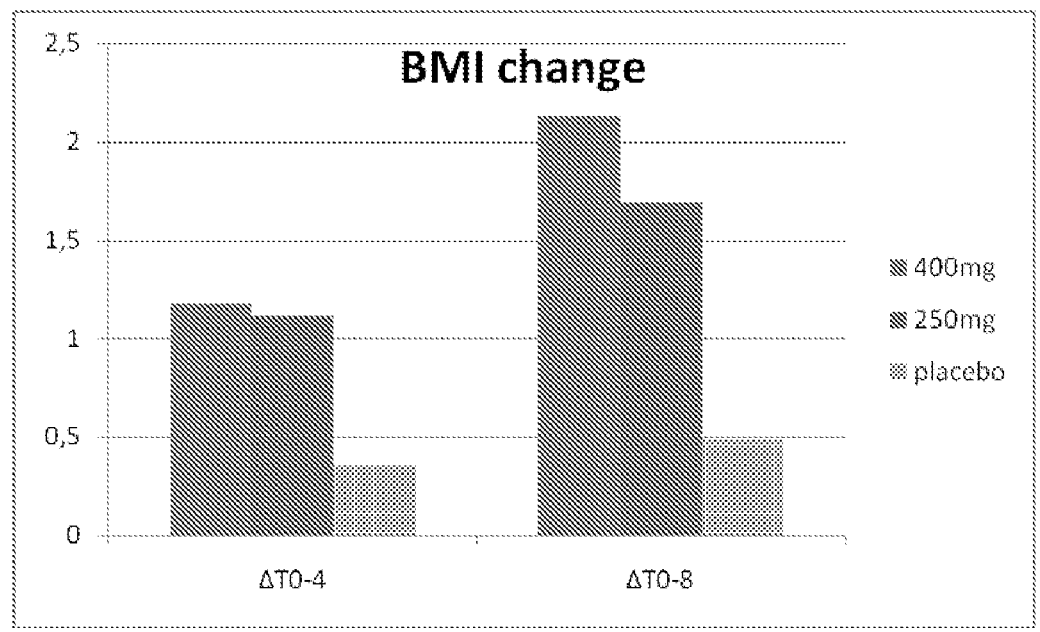
Figure 3A:
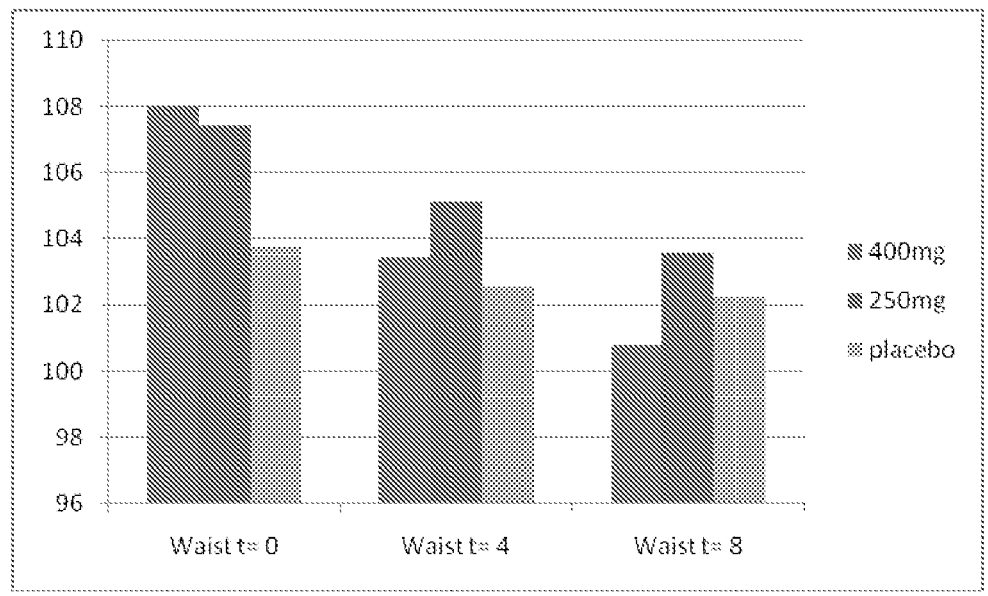
FIGS. 3A and 3B are bar graph charts which graphically demonstrate the results of waist change after administering DG as part of the experiments described herein.
Figure 3B:
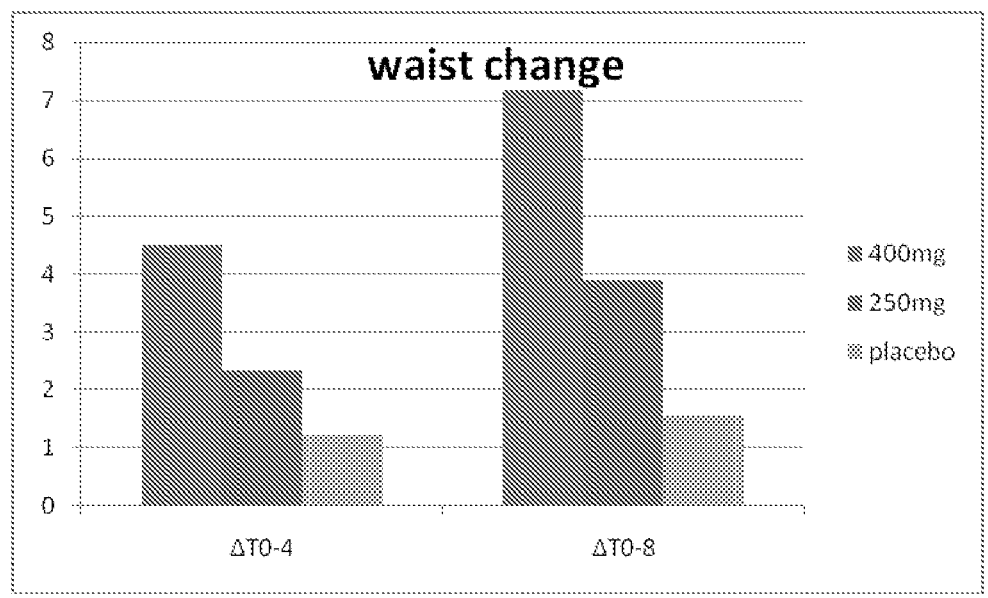
Figure 4A:
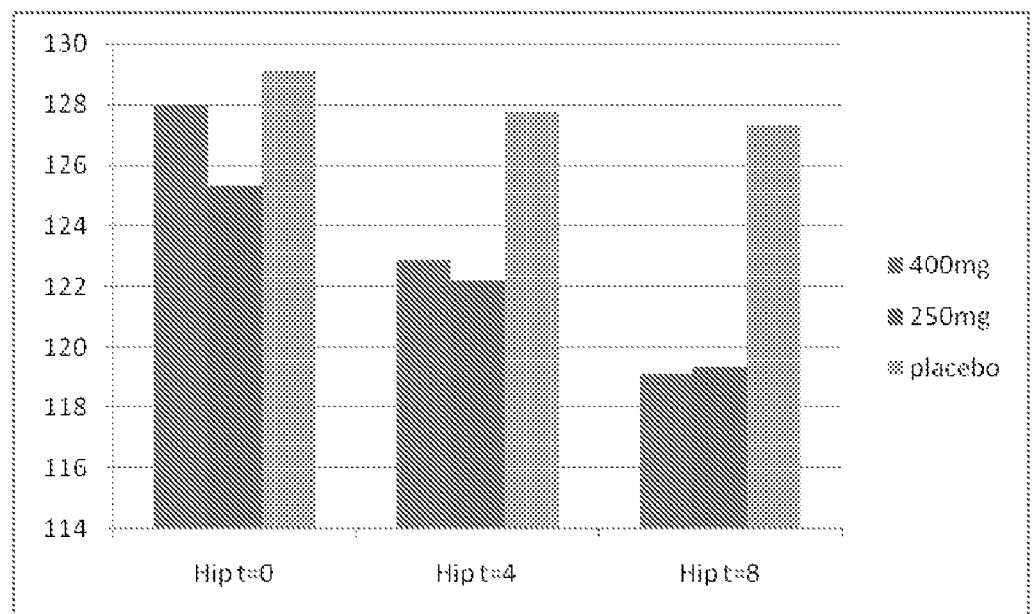
FIGS. 4A and 4B are bar graph charts which graphically demonstrate the results of hip change after administering DG as part of the experiments described herein.
Figure 4B:
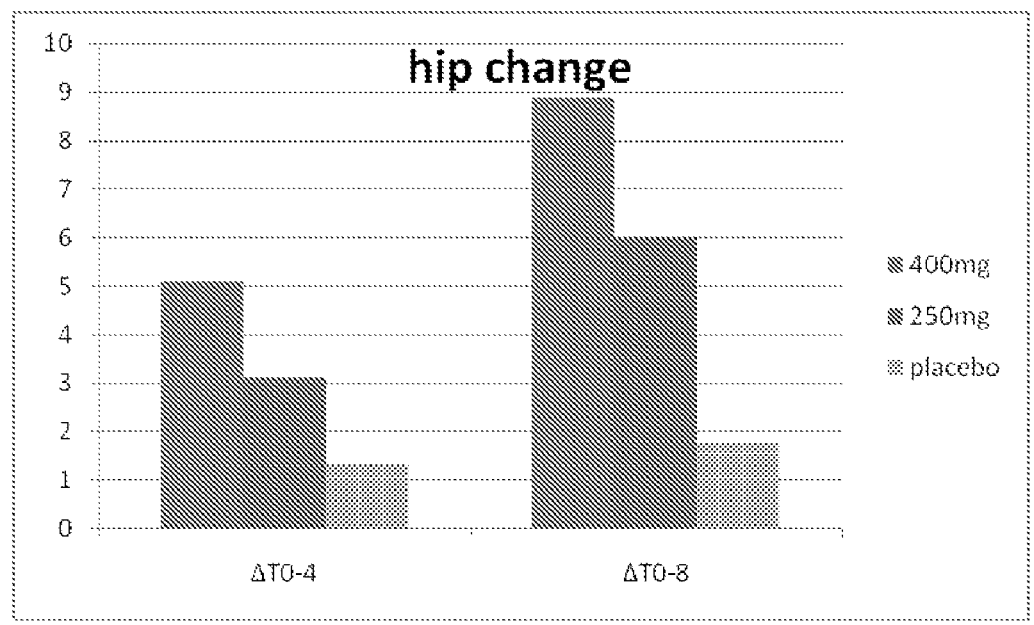
Figure 5A:
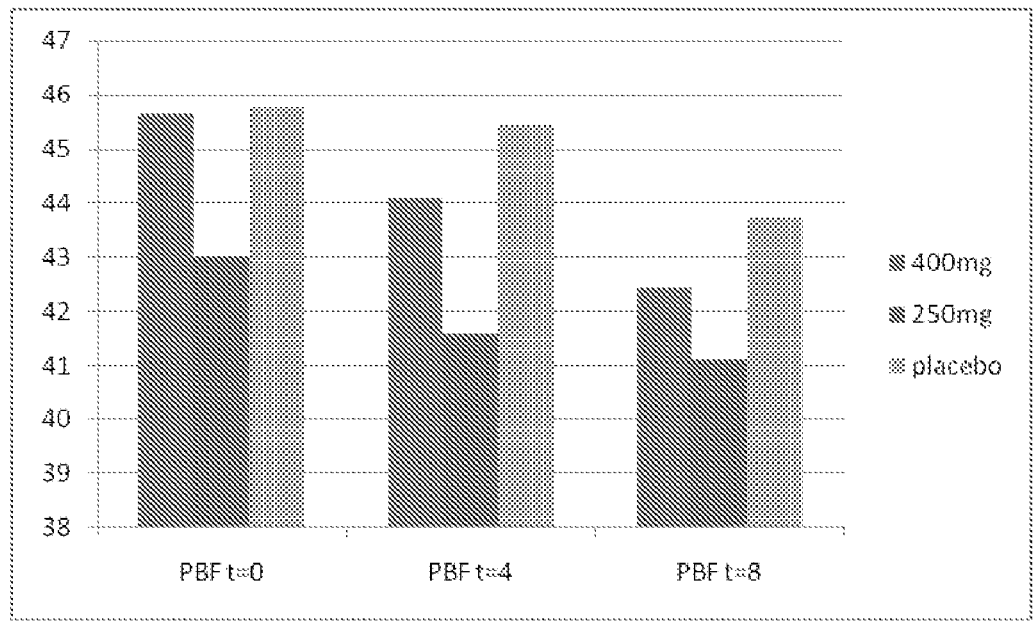
FIGS. 5A and 5B are bar graph charts which graphically demonstrate the results of PBF change after administering DG as part of the experiments described herein.
Figure 5B:
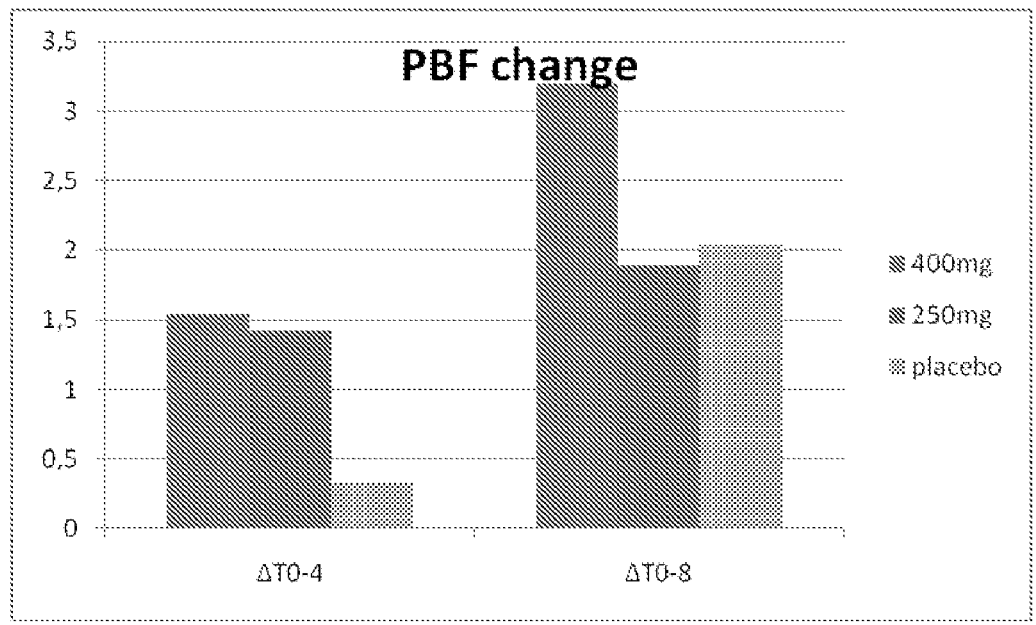
Figure 6A:
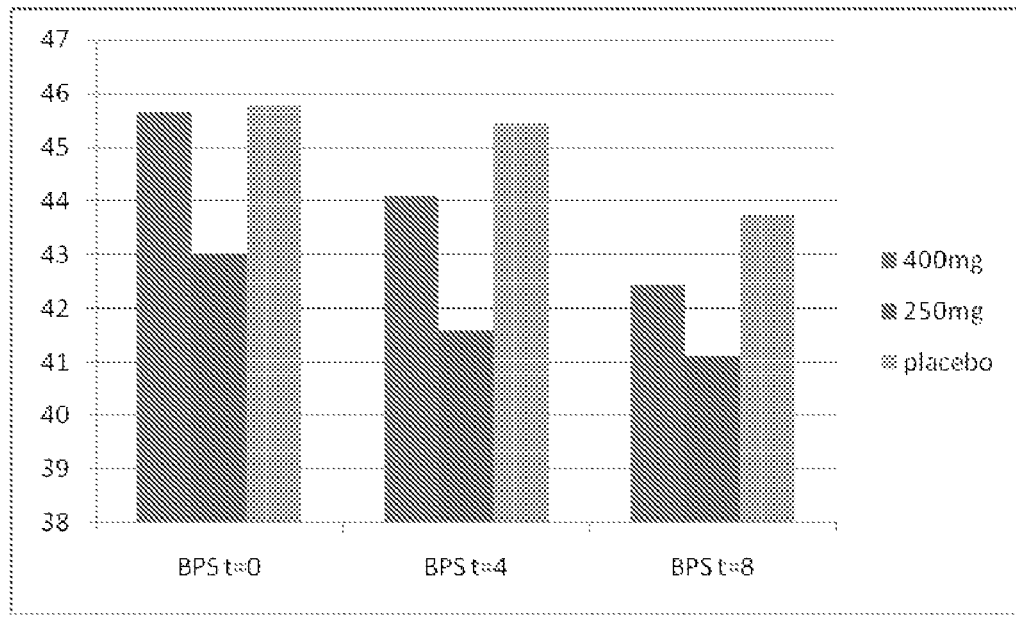
FIGS. 6A and 6B are bar graph charts which graphically demonstrate the results of BPS (systolic blood pressure) change after administering DG as part of the experiments described herein.
Figure 6B:
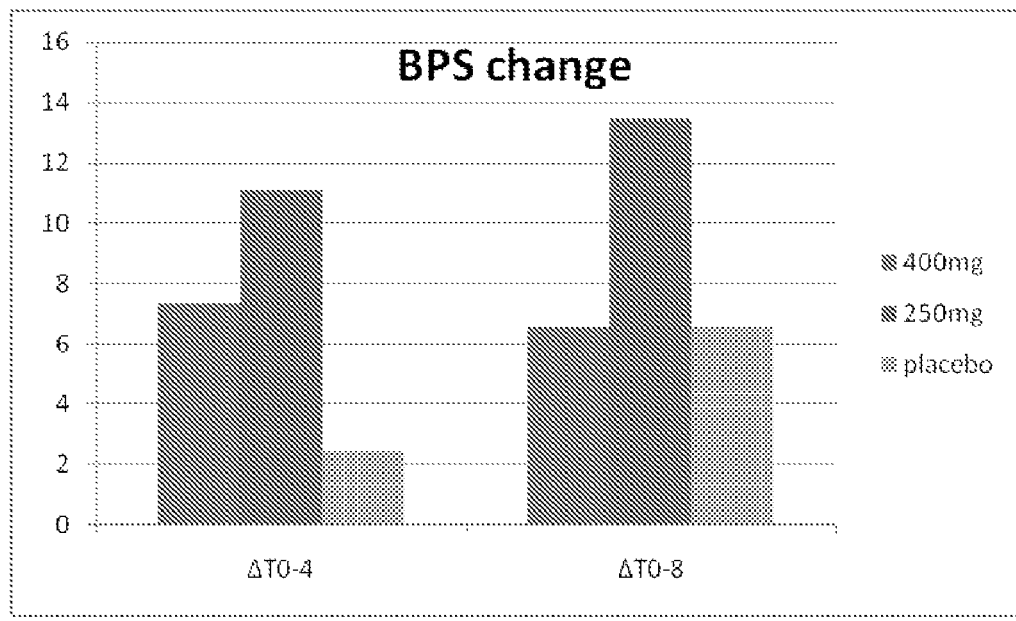
Figure 7A:
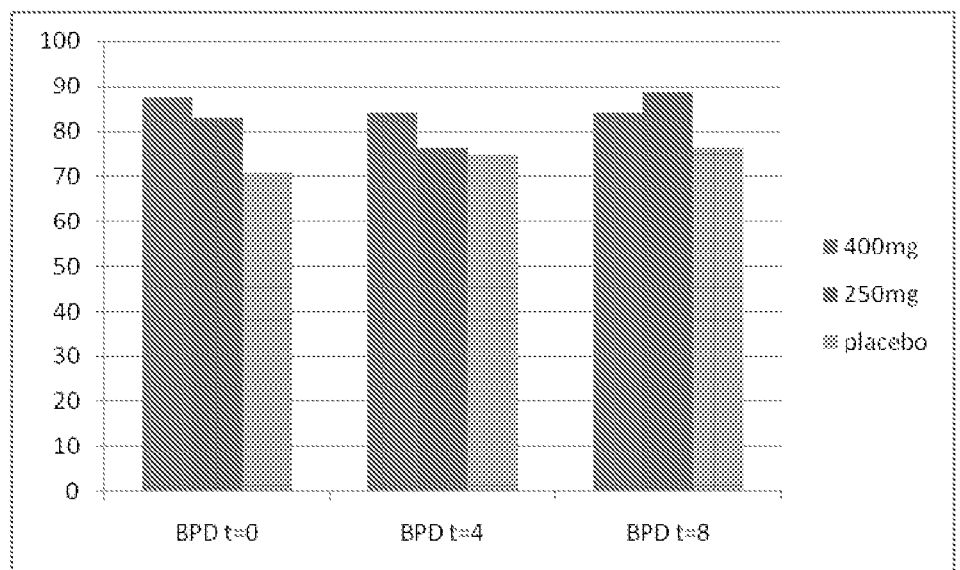
FIGS. 7A and 7B are bar graph charts which graphically demonstrate the results of BPD (diastolic blood pressure) change after administering DG as part of the experiments described herein.
Figure 7B:
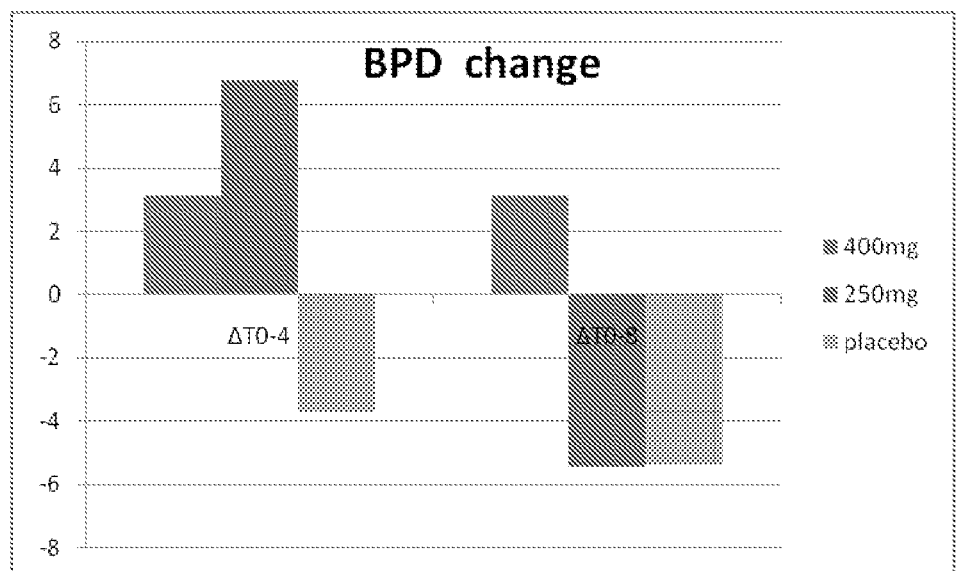
Figure 8A:
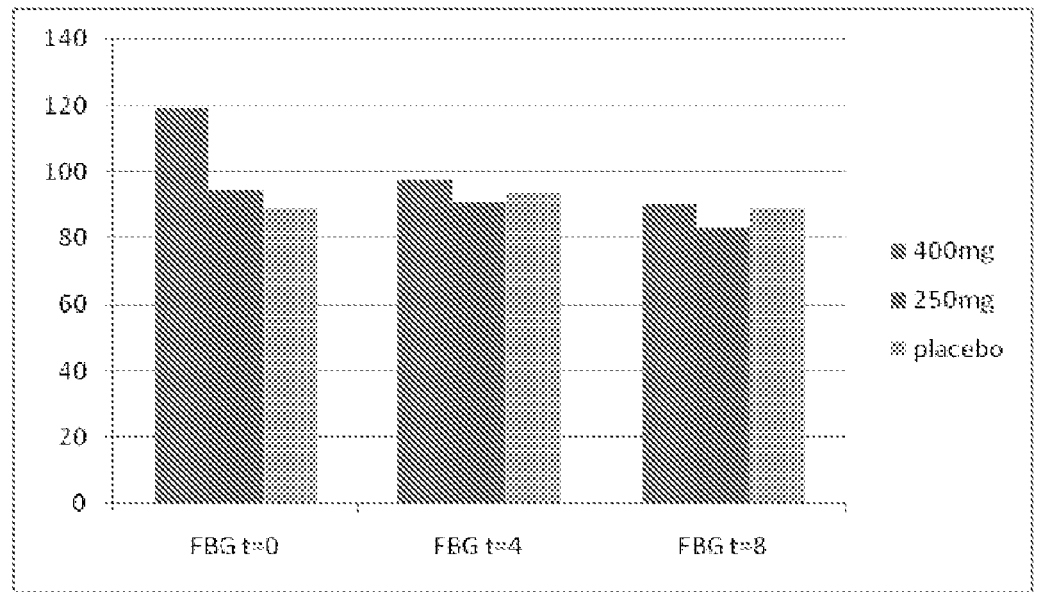
FIGS. 8A, 8B, and 8C are bar graph charts which graphically demonstrate the results of FBG (fasting blood glucose) after administering DG as part of the experiments described herein.
Figure 8B:
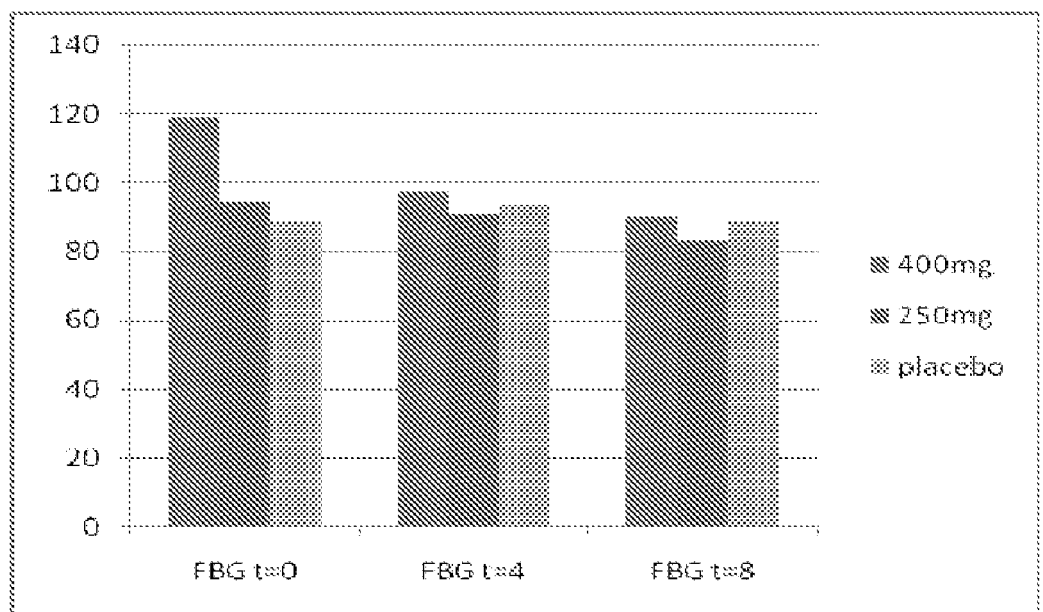
Figure 8C:
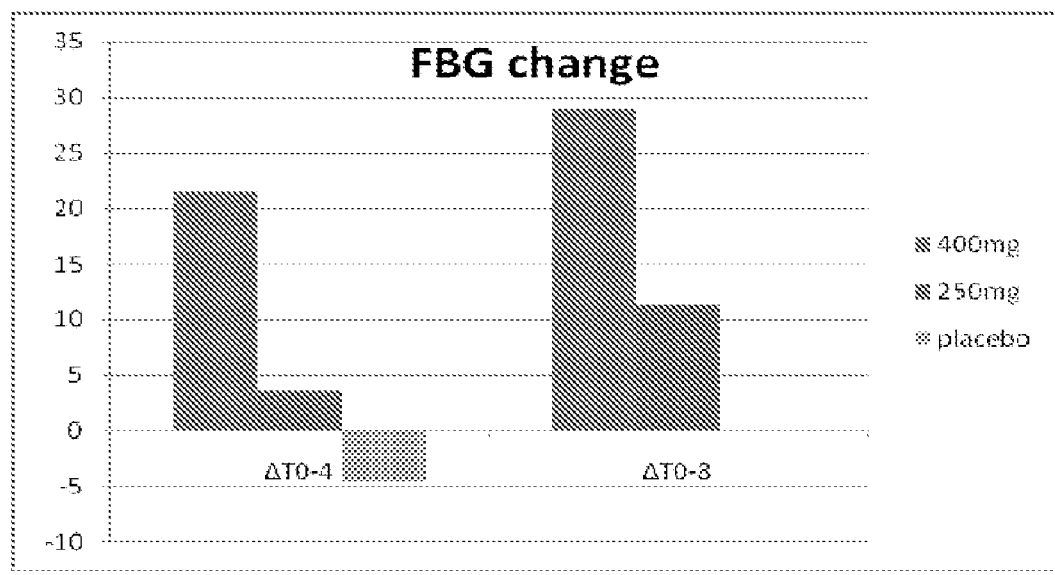
Figure 9A:
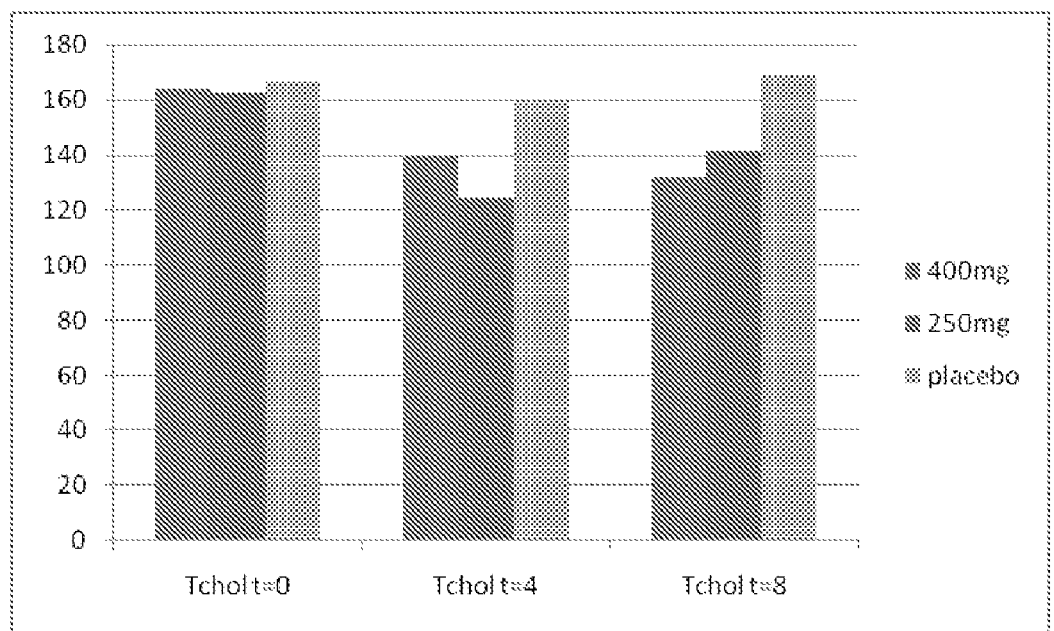
FIGS. 9A and 9B are bar graph charts which graphically demonstrate the results of tcho change after administering DG as part of the experiments described herein.
Figure 9B:
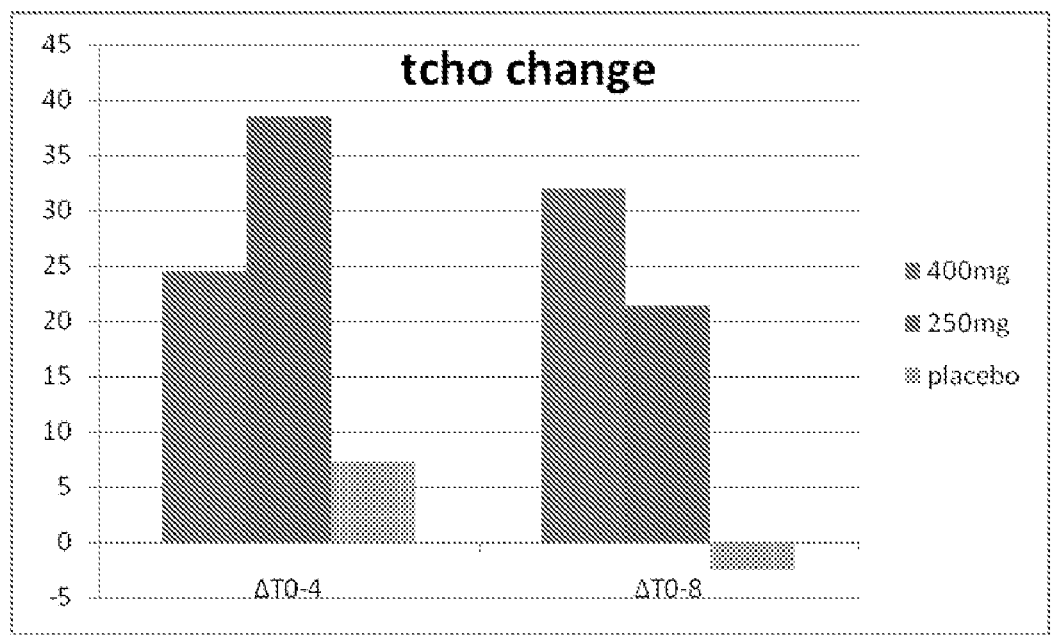
Figure 10A:
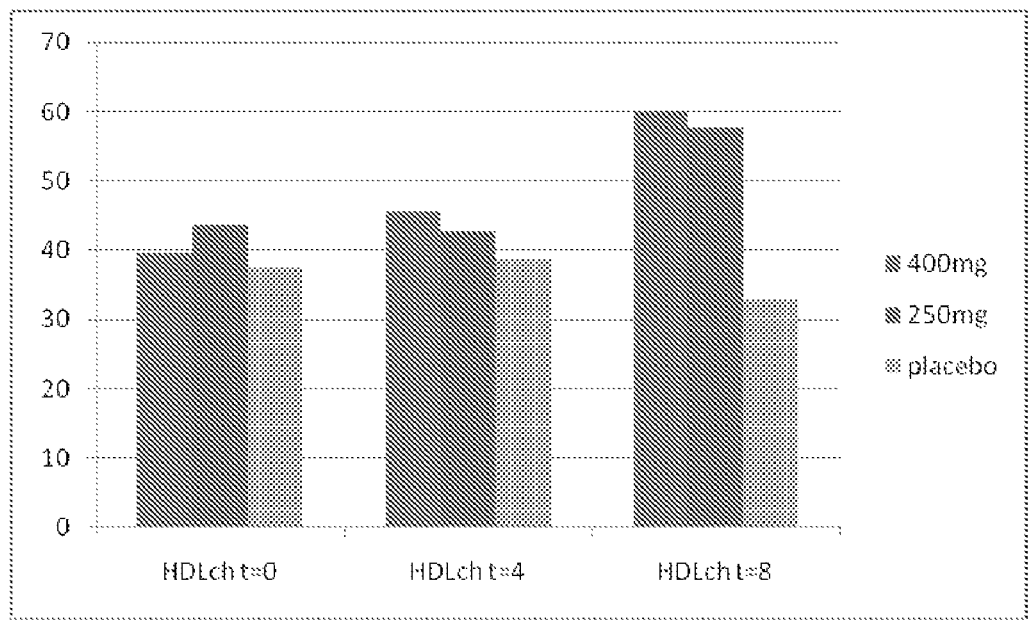
FIGS. 10A and 10B are bar graph charts which graphically demonstrate the results of HDLch change after administering DG as part of the experiments described herein.
Figure 10B:
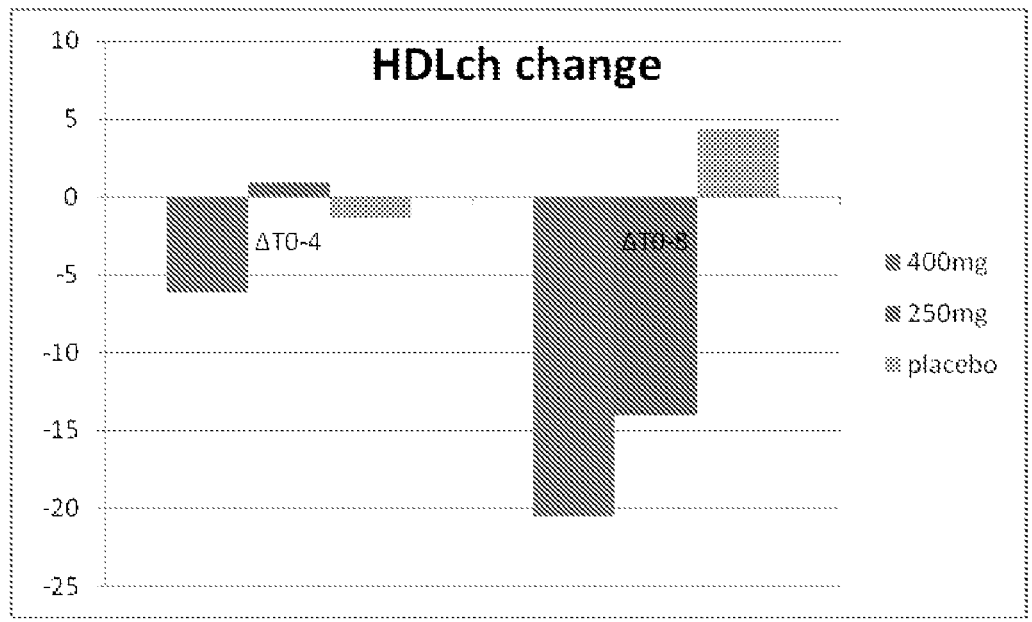
Figure 11A:
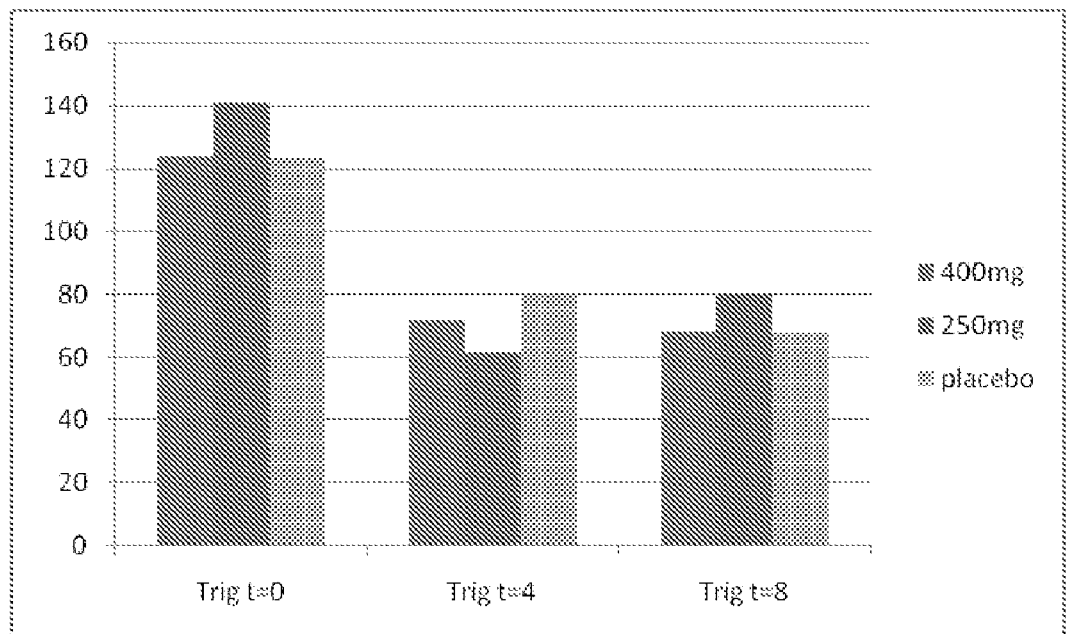
FIGS. 11A and 11B are bar graph charts which graphically demonstrate the results of changes in triglyceride levels after administering DG as part of the experiments described herein.
Figure 11B:
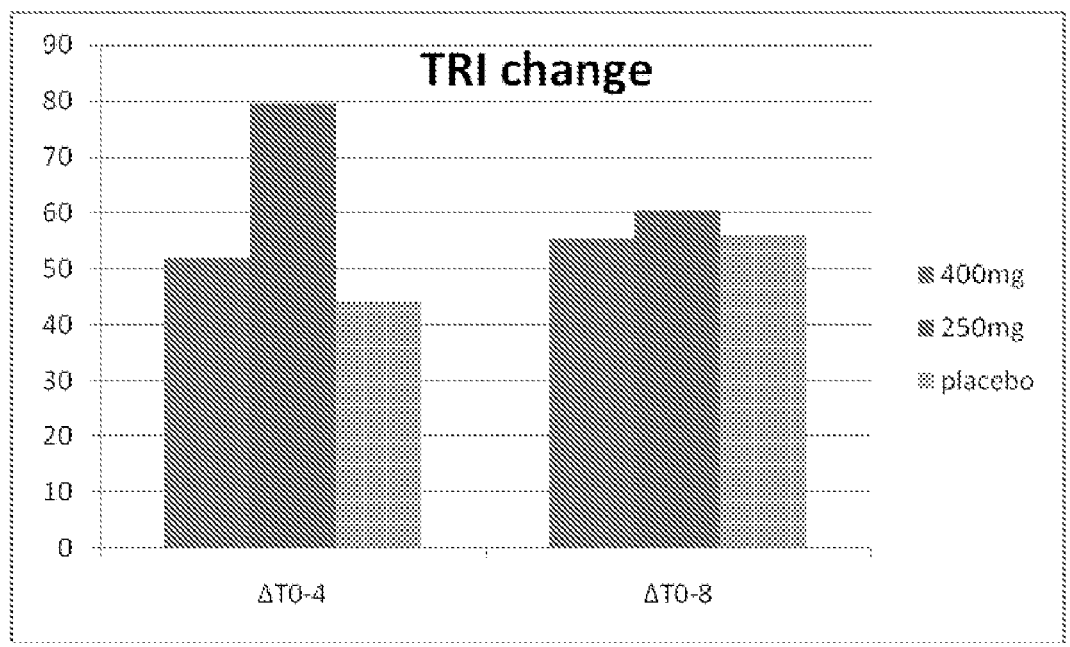
Figure 12A:
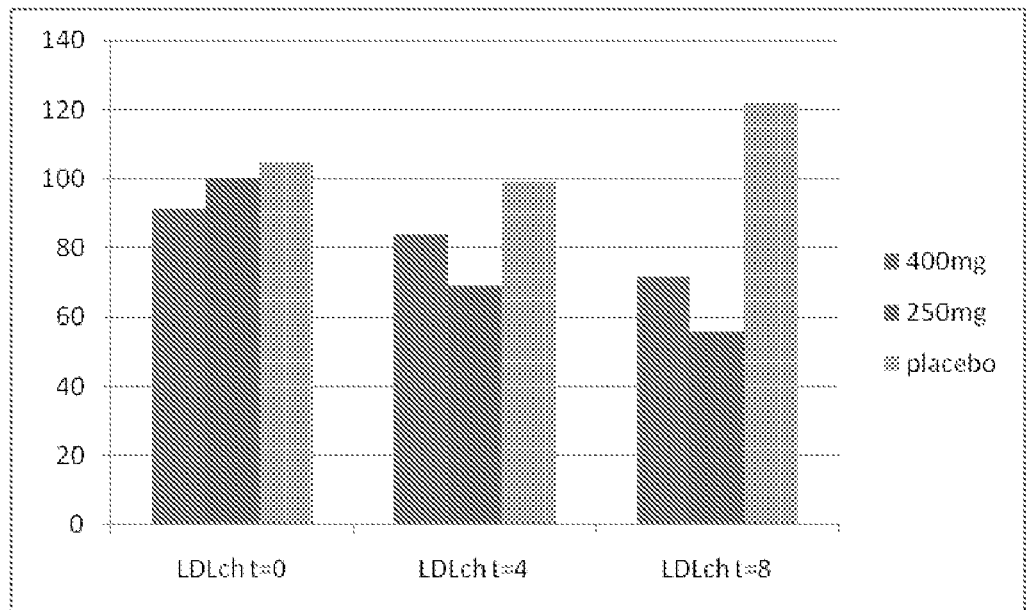
FIGS. 12A and 12B are bar graph charts which graphically demonstrate the results of changes in LDL levels after administering DG as part of the experiments described herein.
Figure 12B:
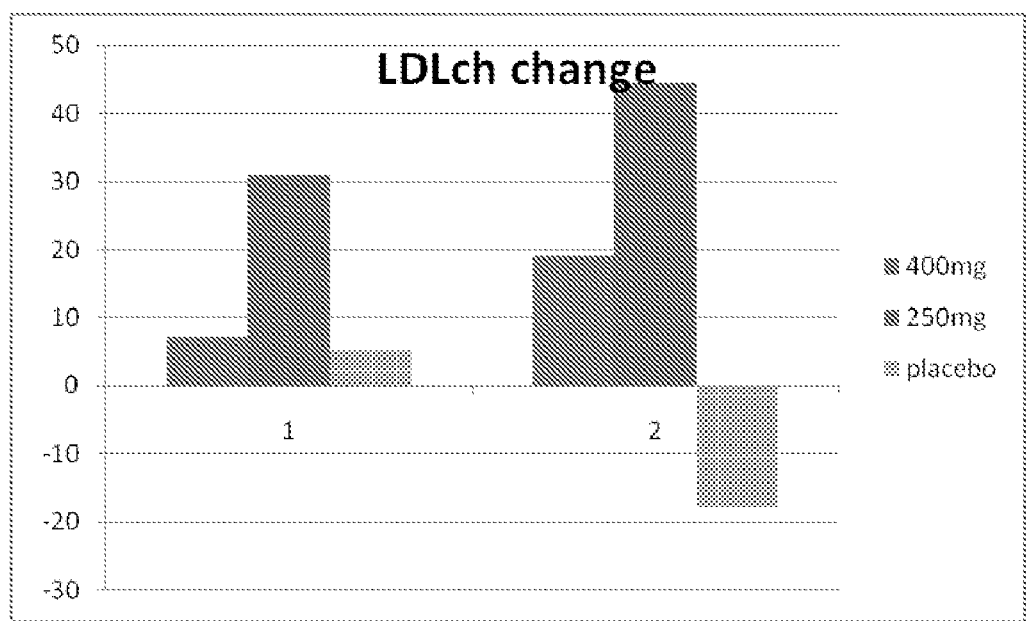
Figure 13:
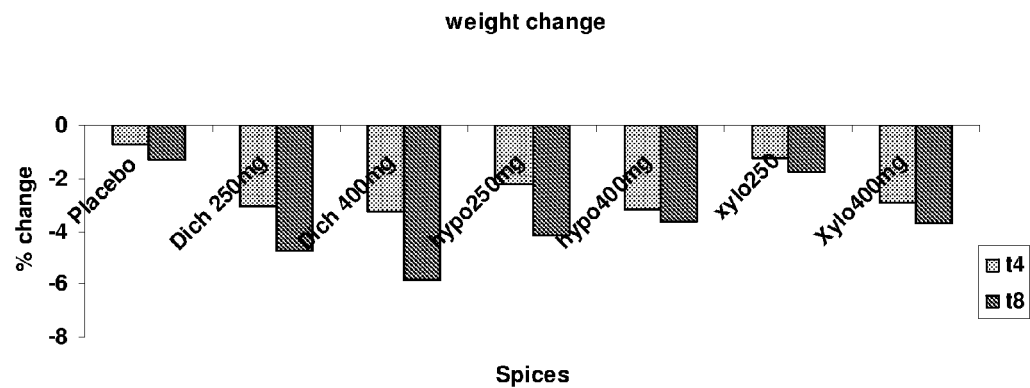
FIG. 13 is bar graph chart which graphically demonstrates the changes in waist measurements after administering the indicated DG, XA and HZ as part of the experiments described herein. The results demonstrate that after 4 and 8 weeks of treatment, all the treated subjects (except the XA 250 mg treated subjects) significantly ($P<0.05$) lost more weight than the placebo group.
Figure 14:
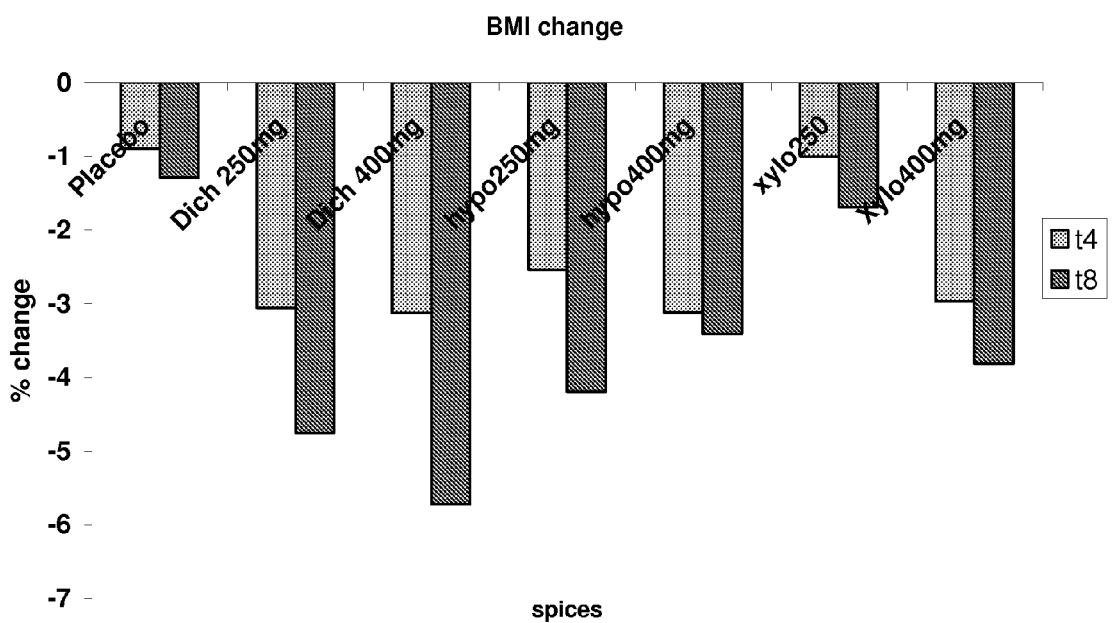
FIG. 14 is bar graph chart which graphically demonstrates the changes in BMI as determined during the experiments described herein. The results demonstrate that the BMI was significantly reduced in all groups (except the XA1 group) over the study period.
Figure 15:
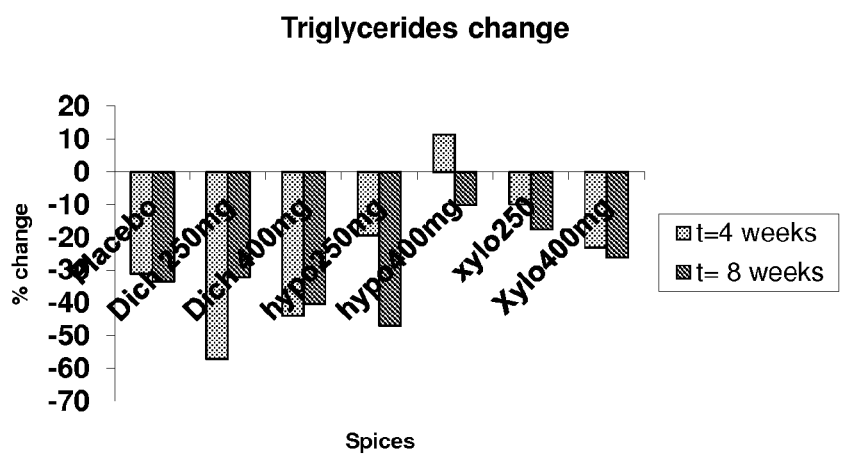
FIG. 15 is bar graph chart which graphically demonstrates the changes in plasma triglyceride levels as determined during the experiments described herein. The results demonstrate shows that only the DG 1 group showed a significant reduction in plasma triglycerides during the first four weeks of treatment. At the end, of the experiment, only the HZ1 group showed a significant ($P>0.05$) reduction of plasma triglycerides compared to the placebo group.
Figure 16:
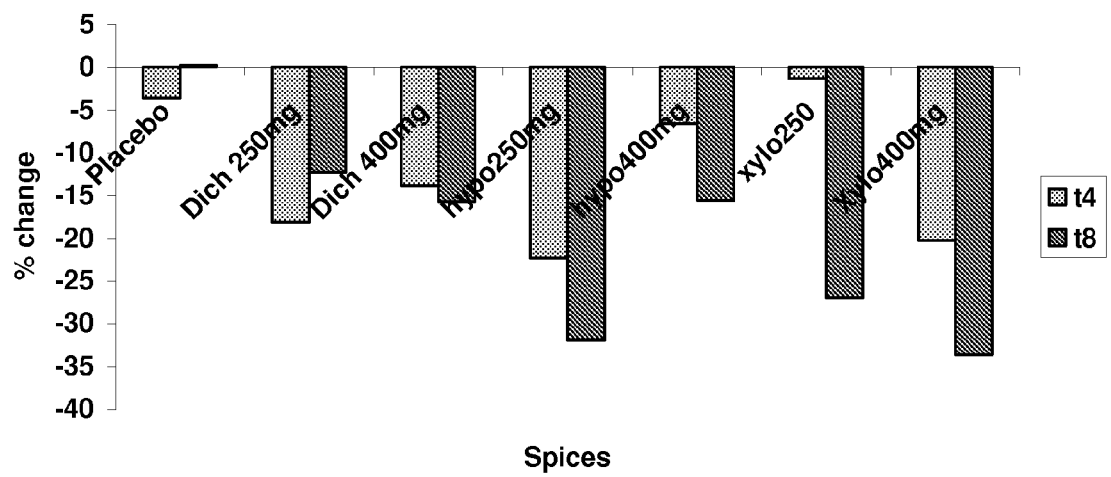
FIG. 16 is bar graph chart which graphically demonstrates the changes in total cholesterol levels as determined during the experiments described herein. The results demonstrate that during the first four weeks of treatment, all the treated subjects (except the XA1 group) showed a significant reduction of plasma total-cholesterol, while after 8 weeks, the reduction was observe in all groups.
Figure 17:
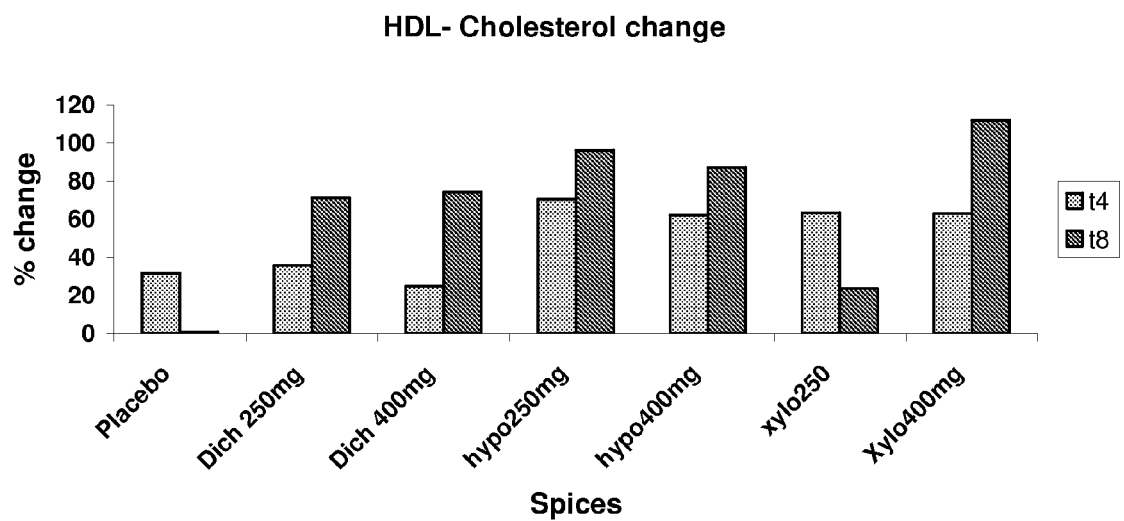
FIG. 17 is bar graph chart which graphically demonstrates the changes in HDL cholesterol levels as determined during the experiments described herein. The results demonstrate shows that both HZ groups and the XA2 group had the most significant increases in HDL-cholesterol levels after 4 and 8 weeks of treatment.
Figure 18:
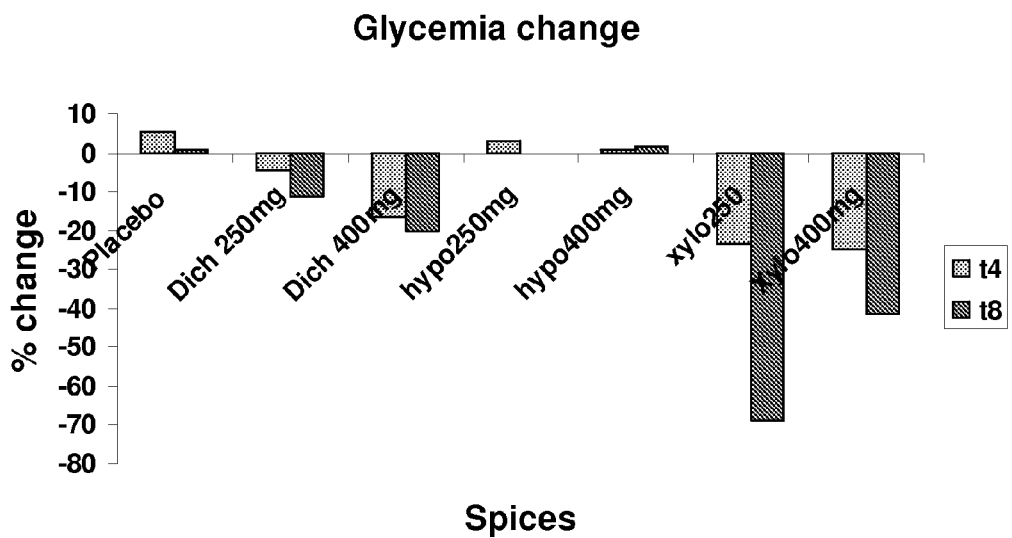
FIG. 18 is bar graph chart which graphically demonstrate the changes in waist measurements as determined during the experiments described herein. The results demonstrate that the XA groups brought about the most significant decreases in fasting blood glucose levels.
Figure 19:
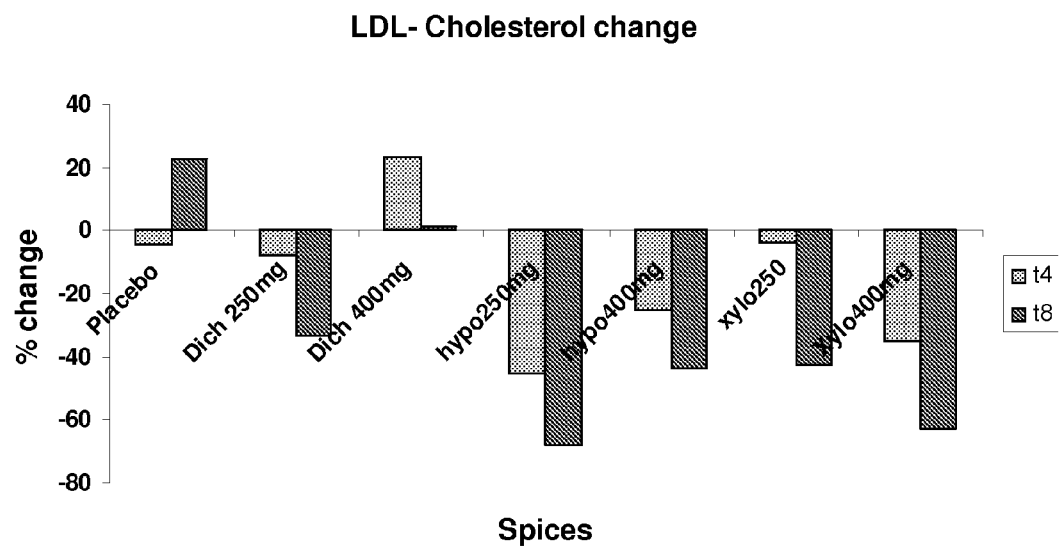
FIG. 19 is bar graph chart which graphically demonstrate the changes in LDL cholesterol levels as determined during the experiments described herein. The results demonstrate shows that at the end of the experiment, all the treated groups (except DG2) brought about a significant reduction of LDL-cholesterol compared to the placebo group.
Figure 20:
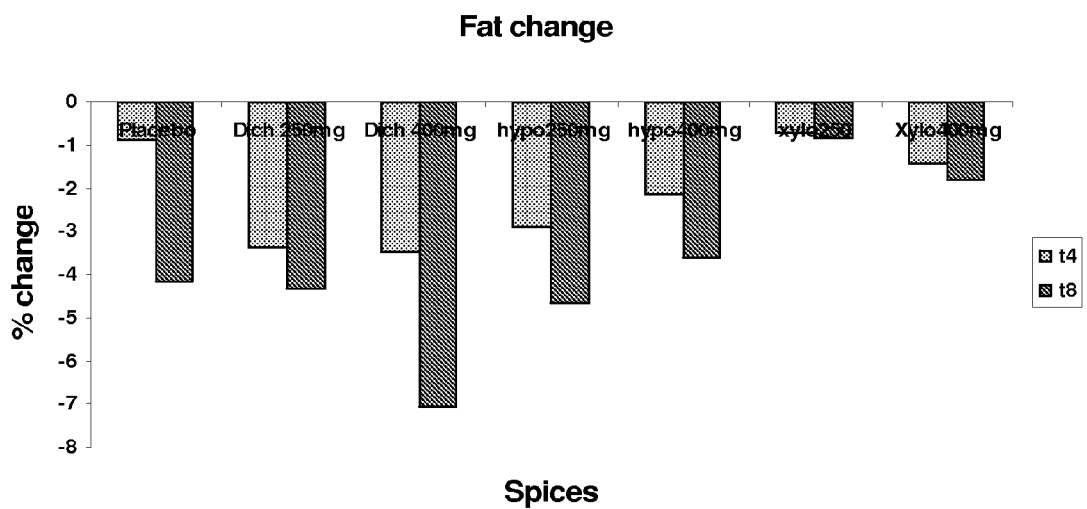
FIG. 20 is bar graph chart which graphically demonstrate the changes in percentage body fat as determined during the experiments described herein. The results demonstrate that the percentage body fat was most altered in the DG2 group.
Figure 21:
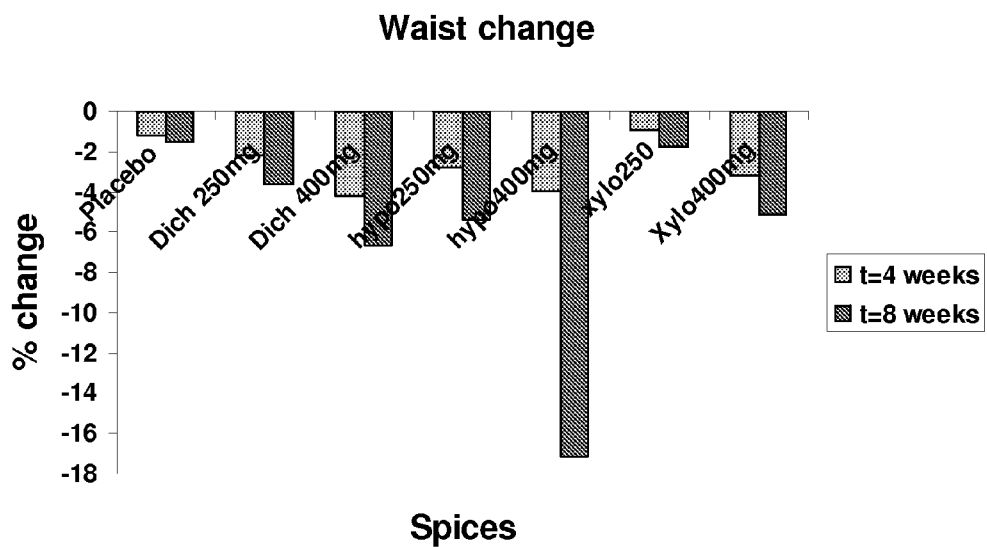
FIG. 21 is bar graph chart which graphically demonstrate the changes in waist circumference as determined during the experiments described herein. The results demonstrate that the most significant reduction in waist circumference was in the HP2 group.
Figure 22:
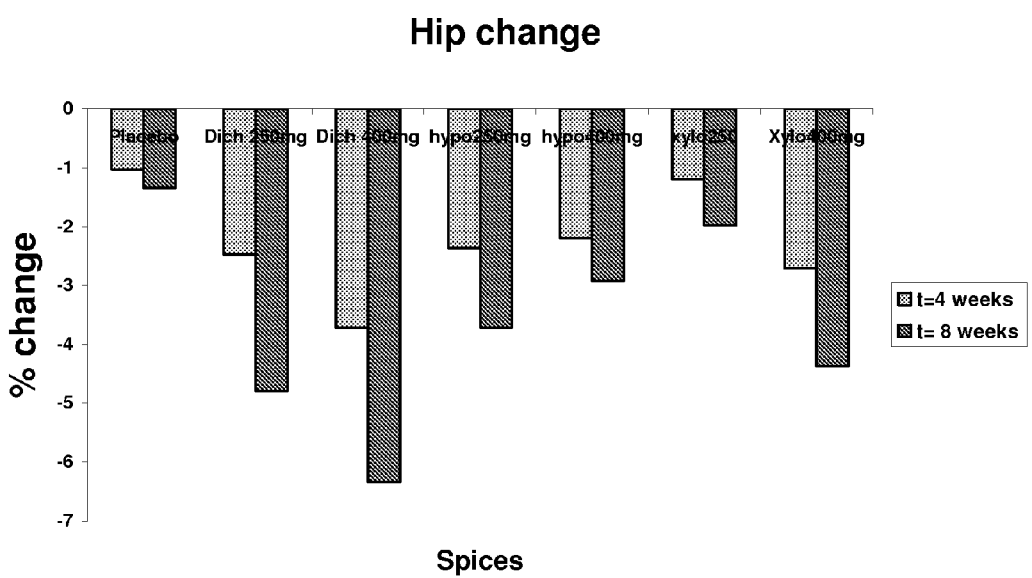
FIG. 22 is bar graph chart which graphically demonstrate the changes in hip circumference as determined during the experiments described herein. The results demonstrate the percentage of change in hip circumference.
Figure 23:
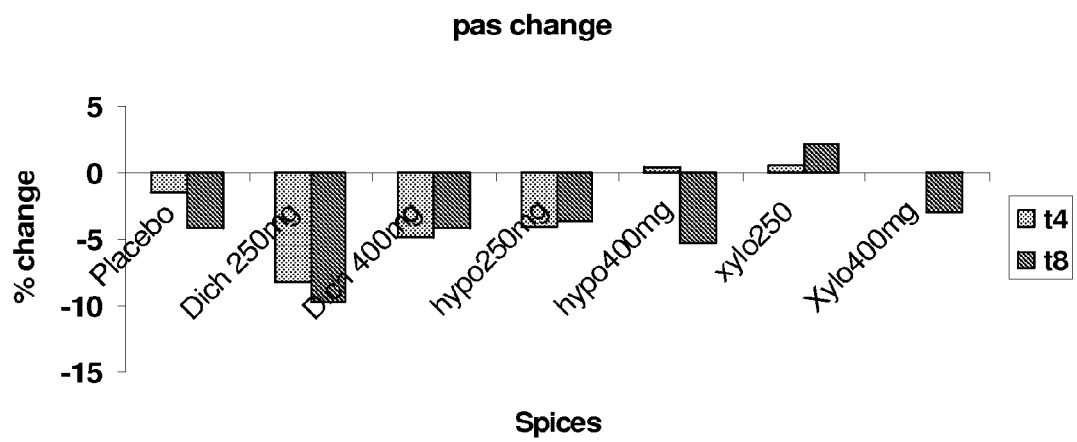
FIG. 23 is bar graph chart which graphically demonstrate the changes in systolic blood pressure as determined during the experiments described herein. The results demonstrate that the most significant decrease in systolic blood pressure was in the DG I group.
Figure 24:
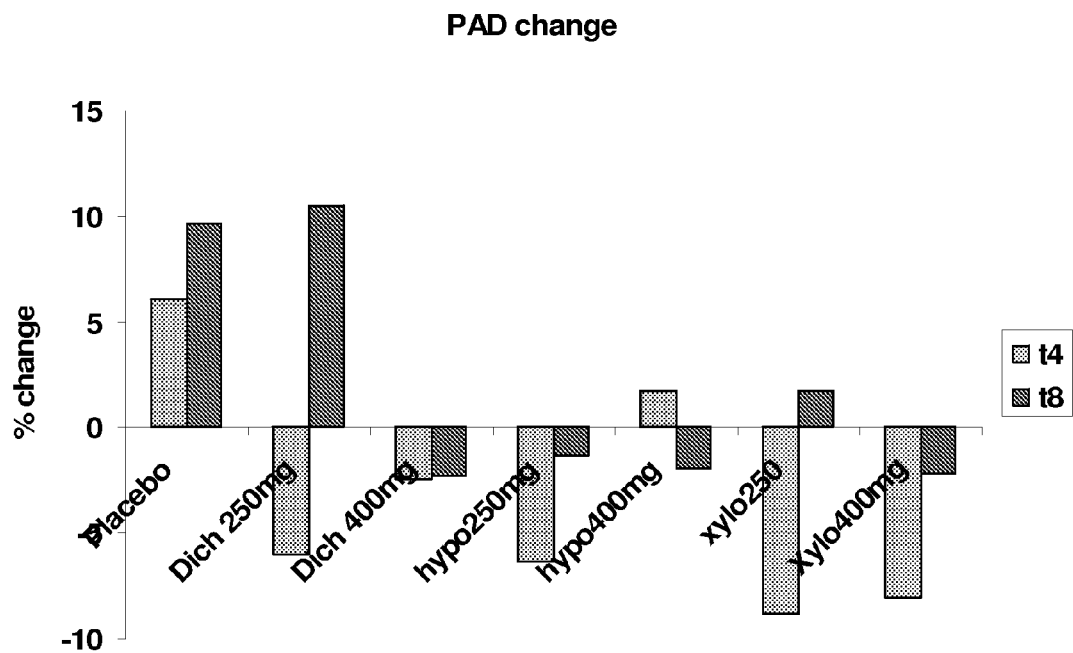
FIG. 24 is bar graph chart which graphically demonstrate the changes in diastolic blood pressure as determined during the experiments described herein. The results demonstrate shows that diastolic blood pressure was significantly reduced in all groups except the DG I group.

The results discussed herein and demonstrated in FIGS. 1-24 of the present application are for human subjects (6 per group) who were on either placebo or two different doses (2×250 or 2×400 mg) of the ground spice daily over an 8-week period.

The results clearly show a positive effect on a variety of health related factors, more specifically, anthropometric as well as blood lipid parameters, all of which are within the scope of the present inventions.

In one embodiment of the present disclosure, a method of reducing bodyweight in an otherwise healthy overweight subject, the method comprising: administering a composition containing an effective amount of *Hypodaphnis zenkeri* to the overweight subject.

In another embodiment of the present disclosure, a method of reducing bodyweight in an otherwise healthy overweight subject, wherein the effective amount is 200 mg to 6000 mg to the overweight subject per day.

In one aspect of at least one another embodiment of the present disclosure, a method of reducing bodyweight in an otherwise healthy overweight subject, wherein the composition comprises the seed of the *Hypodaphnis zenkeri*.

In another aspect of at least one embodiment of the present disclosure, a method of reducing bodyweight in an otherwise healthy overweight subject, wherein the composition comprises the bark of *Hypodaphnis zenkeri*.

In yet another aspect of at least one embodiment of the present disclosure, a method of reducing bodyweight in an otherwise healthy overweight subject, wherein the composition comprises ground-up *Hypodaphnis zenkeri* plant.

In yet another aspect of at least one embodiment of the present disclosure, a method of reducing bodyweight in an otherwise healthy overweight subject, wherein the composition comprises the pods of *Hypodaphnis zenkeri*.

In yet another aspect of at least one embodiment of the present disclosure, a method of reducing bodyweight in an otherwise healthy overweight subject, wherein the pods are dried ground pods.

It should be appreciated that the inventions of the present disclosure include administration of *Dichrostachys glomerata* (DG), *Hypodaphnis zenkeri* (HZ) and/or *Xylopia aethiopica* (XA) to improve any of the health related factors and related conditions for which data is provided herein.

The bibliography articles referenced herein and listed below, in no particular order, are related to the present disclosure, the contents of which are expressly incorporated herein in their entirety.

Goldstein D J. (1992): Beneficial health effects of modest weight loss. Int JObes Relat Metab Disord.; 16:397-415.

Williamson D. (1997): Intentional weight loss. Int JObes Relat Metab Disord.; 21(suppll):S 14-S 19.

Srinivasan (2005): Role of Spices Beyond Food Flavoring: Nutraceuticals with Multiple Health Effects.

Joe, B., & Lokesh, B. R. (1994): Role 0 capsaicin, curcumin and dietary n_3 fatty acids in lowering the generation of reactive oxygen species in rat peritoneal macrophages. Biochimica Biophysica Acta, 1224, 255-263.

Reddy, A. C. P., & Lokesh, B. R. (1994c). Alterations in lipid peroxidation in rat liver by dietary n_3 fatty acids: modulation of antioxidant enzymes by curcumin, eugenol and vitamin-E. Journal of Nutritional Biochemistry, 5, 181-188.

Bachorik P S, Wood P D, Alers J J, Steiner P, Dempsey M, Kuba K, Warnick R, Karlsson L: Plasma high-density cholesterol concentrations determined after removal of other lipoproteins by heparin/manganese precipitation or by ultracentrifugation. Clin Chern 1976, 22: 1828-1834.

Friedewald W T, Levy R I, Fredrickson DS: Estimation of the concentration of low-density lipoprotein cholesterol in plasma, without use of the preparative ultracentrifuge. Clin Chern 1972, 18(6):449-502.

Trinder P, (1969). Determination of glucose in blood using glucose oxidase with an alternative oxygen acceptor. Ann. Clin. Biochem. 6, 24.

Richmond W, (1973). Preparation and properties of a cholesterol oxidase from *Nocardia* sp. and its application to the enzymatic assay of total cholesterol in serum. Clin Chern 19, 1350-1356.

Buccolo G., David H, (1973). Quantitative determination of serum triglycerides by the use of enzymes. Clin. Chern. 19, 476-482.

Kenneth F. Adams, Arthur Schatzkin, Tamara B. Harris, Victor Kipnis, Traci Mouw, Rachel Ballard-Barbash, Albert Hollenbeck, and Michael F. Leitzmann (2006). Overweight, Obesity, and Mortality in a Large Prospective Cohort of Persons 50 to 71 Years Old. New Engl. J. Med. 355, 763-778.

Peter, K. V. Handbook of Herbs and Spices Volume Three edited by K. V. Peter, 2006.

The present disclosure embodies inventions covered by any combination or portion of one or more aspects of the present disclosure and/or one or more of the following elements alone or in combination with one or more aspects of the present disclosure.

What is claimed is:

1. A method of reducing bodyweight in an otherwise healthy overweight subject, the method comprising: administering a composition containing an effective amount of *Hypodaphnis zenkeri* to the overweight subject.

2. The method of claim 1, wherein the effective amount is 200 mg to 6000 mg to the overweight subject per day.

3. The method of claim 1, wherein the composition comprises the seed of the *Hypodaphnis zenkeri*.

4. The method of claim 1, wherein the composition comprises the bark of *Hypodaphnis zenkeri*.

5. The method of claim 1, wherein the composition comprises ground-up *Hypodaphnis zenkeri* plant.

6. The method of claim 1, wherein the composition comprises the pods of *Hypodaphnis zenkeri*.

7. The method of claim 6, wherein the pods are dried ground pods.

\* \* \* \* \*